United States Patent
Dubois et al.

(10) Patent No.: US 9,408,792 B2
(45) Date of Patent: Aug. 9, 2016

(54) ISOCHRYSIS SP TAHITIAN CLONE AND USES THEREFORE

(75) Inventors: Nolween Dubois, Nantes (FR); Jean-Paul Cadoret, Basse Goulaine (FR); Gael Bougaran, Nantes (FR); Catherine Rouxel, Orvault (FR); Sophie Doulin, Sainte Euphemie (FR)

(73) Assignee: INSTITUT FRANCAIS DE RECHERCHE POUR L'EXPLOITATION DE LA MER (IFREMER), Issy-les-Moulineaux Cedex (FR)

(*) Notice: Subject to any disclaimer, the term of this patent is extended or adjusted under 35 U.S.C. 154(b) by 0 days.

(21) Appl. No.: 14/239,290

(22) PCT Filed: Aug. 16, 2012

(86) PCT No.: PCT/EP2012/003491
§ 371 (c)(1),
(2), (4) Date: May 15, 2014

(87) PCT Pub. No.: WO2013/023786
PCT Pub. Date: Feb. 21, 2013

(65) Prior Publication Data
US 2014/0310827 A1 Oct. 16, 2014

(30) Foreign Application Priority Data
Aug. 17, 2011 (EP) .................................... 11006712

(51) Int. Cl.
C12N 1/12 (2006.01)
A61K 8/37 (2006.01)
C12R 1/89 (2006.01)
A23L 1/30 (2006.01)
A61K 8/36 (2006.01)
A61Q 19/00 (2006.01)
A61Q 19/08 (2006.01)
C10L 1/02 (2006.01)

(52) U.S. Cl.
CPC ................. *A61K 8/37* (2013.01); *A23L 1/3006* (2013.01); *A61K 8/361* (2013.01); *A61Q 19/00* (2013.01); *A61Q 19/007* (2013.01); *A61Q 19/08* (2013.01); *C10L 1/02* (2013.01); *C12N 1/12* (2013.01); *C12R 1/89* (2013.01)

(58) Field of Classification Search
CPC ....................................................... C12N 1/12
See application file for complete search history.

(56) References Cited

PUBLICATIONS

Bougran et al., "Transient initial phase in continuous culture of Isochrysis galbana affinis Tahiti," Aquat. Living Resourc. 16:389-394, 2003.*
Bougaran et al., "Transient initial phase in continuous culture of Isochrysis galbana affinis Tahiti," Aquat Living Resour 16(4):389-394, 2003.*
Alonso et al., "Acyl lipid composition variation related to culture age and nitrogen concentration in continuous culture of the microalga Phaeodactylum tricornutum", Phytochemistry, 2000, vol. 54, pp. 461-471.

(Continued)

*Primary Examiner* — Rosanne Kosson
(74) *Attorney, Agent, or Firm* — Young & Thompson

(57) ABSTRACT

A novel microalgal strain whose lipid production has been enhanced compared to the wild type. The lipid content produced by the microalgae is particularly rich in neutral lipids. The use of the microalgal strain and the lipids are also described.

9 Claims, 5 Drawing Sheets

(56) References Cited

PUBLICATIONS

Bougaran et al., "Enhancement of Neutral Lipid Productivity in the Microalga Isochrysis Affinis Galbana (T-Iso) by a Mutation-Selection Procedure", Biotechnology and Bioengineering, 2012, vol. 109, pp. 2737-2745, XP002685486.

Copeman et al., "Effects of docosahexaenoic, eicosapentaenoic, and arachidonic acids on the early growth, survival, lipid composition and pigmentation of yellowtail flounder (Limanda ferruginea): a live food enrichment experiment", Aquaculture, 2002, vol. 210, pp. 285-304.

Fernandez-Reiriz et al., "Effect of Microalgal Diets and Commercial Wheatgerm Flours on the Lipid Profile of Ruditapes decussatus Spat", Comparative Biochemistry and Physiology, 1998, vol. 119A, No. 1, pp. 369-377.

Huerlimann et al., "Growth, Lipid Content, Productivity, and Fatty Acid Composition of Tropical Microalgae for Scale-Up Production", Biotechnology and Bioengineering, 2010, vol. 107, No. 2, pp. 245-257.

Mata et al., "Microalgae for biodiesel production and other applications: A review", Renewable and Sustainable Energy Reviews, 2010, vol. 14, pp. 217-232.

International Search Report, dated Oct. 29, 2012, from corresponding PCT application.

* cited by examiner

ISOCHRYSIS SP TAHITIAN CLONE AND USES THEREFORE

This patent application claims the priority benefit of European Patent Application EP11006712.1 filed on Aug. 17, 2011 which is incorporated herein by reference.

FIELD OF THE INVENTION

The present invention relates to a new microalga strain having enhanced lipid content, and its cosmetic, alimentary and/or energetic uses.

BACKGROUND OF THE INVENTION

Microalgae are marine or freshwater unicellular organisms capable of performing photosynthesis, i.e. using daylight as an energetic source to fix carbon dioxide to grow and thus release oxygen. Thus, microalgae are photoautotrophic organisms.

Microalgae produce approximately half of the atmospheric oxygen. Microalgae are also important in the food chain. They are the main foodstuff for fish, mollusk and other aquatic animals.

Microalgae are at the heart of many research and programs and many start-ups have been launched with the aim of developing and exploiting their capacities.

Microalgal production worldwide has doubled in five years, from 5000 tons to 10000 tons (van Harmelen & Oonk, 2006).

There are thousands of catalogued microalga species, although only a few of them are commercially exploited. The main requirements a microalga species must meet to be susceptible of industrial use are suitable growth and a different biochemical composition conferring it the highest possible added value. In this sense, the microalga species that are commercially exploited today range from *Chlorella* and *Nannochloropsis* for aquaculture (Borowitzka, Journal of Biotechnology, 70(1-3), (1999) 313-321) to *Spirulina* for human consumption (Morist et al., Process Biochemistry, 37(5), (2001), 535-547), or *Dunaliella* and *Haematococcus* for the production of carotenoids such as beta-carotene and astaxanthin, respectively (Guerin et al., Trends in Biotechnology, 21(5), (2003) 210-216).

Microalgae require very few elements to grow, water, nutrients and Sun.

Under particular conditions, microalgae species are known to accumulate fatty acids up to 80% of their dry weight (Christi 2007).

When microalgae growth happens under stress conditions, such as nitrogen deficiency, silica deficiency or other nutrient deficiencies, microalgae accumulate high quantities of neutral lipids, especially triacylglycerol (TAG).

TAG are called neutral lipids because they don't carry charged group, contrary to phospholipids or glycolipids. TAG are apolar lipids. Thus, they are insoluble in water.

TAG are a combination of 3 fatty acids and a glycerol molecule. They are stored in vegetal organisms and animal fat tissues and mainly used as an energy reserve.

TAG can have different industrial uses. A growing use of TAG is the production of biodiesel by a transesterification but for the moment, this use is very expensive.

Fatty acids can be saturated, monounsaturated or polyunsaturated.

Poly unsaturated fatty acids (PUFAs) are the most interesting fatty acids, because of their benefits for human health. They have properties that permit to lower cholesterol level and atherogenesis risk.

Among the PUFAs of interest potentially produced by microalgae, there are omega-3 fatty acids. Omega-3 fatty acids are Cis-polyunsaturated fatty acids. They are essential fats, that means that the human body can't synthetize them.

In particular, docosahexaenoic acid (DHA) has been identified as having a major role in the prevention of many of the ailments which afflict modern society eg ischaemic heart disease, rheumatoid arthritis and associated conditions and the degeneration of tissue function. The specific role of DHA has been identified and it is accepted that dietary supplementation with DHA is desirable.

Another omega-3 of interest is eicosapentaenoic acid (EPA). EPA has a major role in the production of prostaglandins, molecules that control blood clotting and other arterial functions. Like DHA, EPA is also known for its benefits for the cardiovascular system.

However, the nutrients deficiencies or the other stress that undergo microalgae to enhance their lipid production often stop their growth and the lipid production at the same time and lead to the consumption of the lipids produced during the growth.

Thus, there remains a need in the art for a way to enhance lipid production in microalgae, preferably production of neutral lipids.

The inventors have obtained a microalgal strain naturally rich in lipids, in particular neutral lipids, which fits to this need.

SUMMARY OF THE INVENTION

The microalgal strain *Isochrysis affinis galbana* Tahitian clone, as disclosed in the present invention, is a microalgal strain that has undergone a selection-mutation process in order to obtain a strain that is richer in lipids than the wild strain. This enhanced lipid content particularly contains more neutral lipids and less phospholipids than the lipid content of the wild strain.

The present invention relates to a strain of the microalga *Isochrysis*, referred to as *Isochrysis affinis galbana* Tahitian clone, deposited within the Culture Collection of Algae and Protozoa (CCAP), SAMS Research Services Ltd, Scottish Marine Institute, OBAN, Argyll PA37 1QA, United Kingdom, Scotland, on Aug. 9, 2011, under accession number CCAP 927/17 or a mutant or variant thereof.

The present invention also relates to a lipid extract obtained from the microalgal strain of the invention.

The present invention also relates to a method of producing the lipid extract of the invention wherein said method comprises the following steps
 a. Culturing the microalgal strain of the invention;
 b. Harvesting the lipid content from said microalgal strain to obtain the lipid extract of the invention.

The present invention also relates to the use of said microalgal strain for producing the lipid extract of the invention.

The present invention also relates to the use of the microalgal strain of the invention in aquaculture.

The present invention also relates to the use of the lipid extract of the invention for producing algofuel.

The present invention also relates to the use of the lipid extract of the invention for producing dietary supplements.

Finally, the present invention relates to the use of the lipid extract of the invention for producing cosmetic compositions.

DETAILED DESCRIPTION OF THE INVENTION

Definitions

Figure 1:
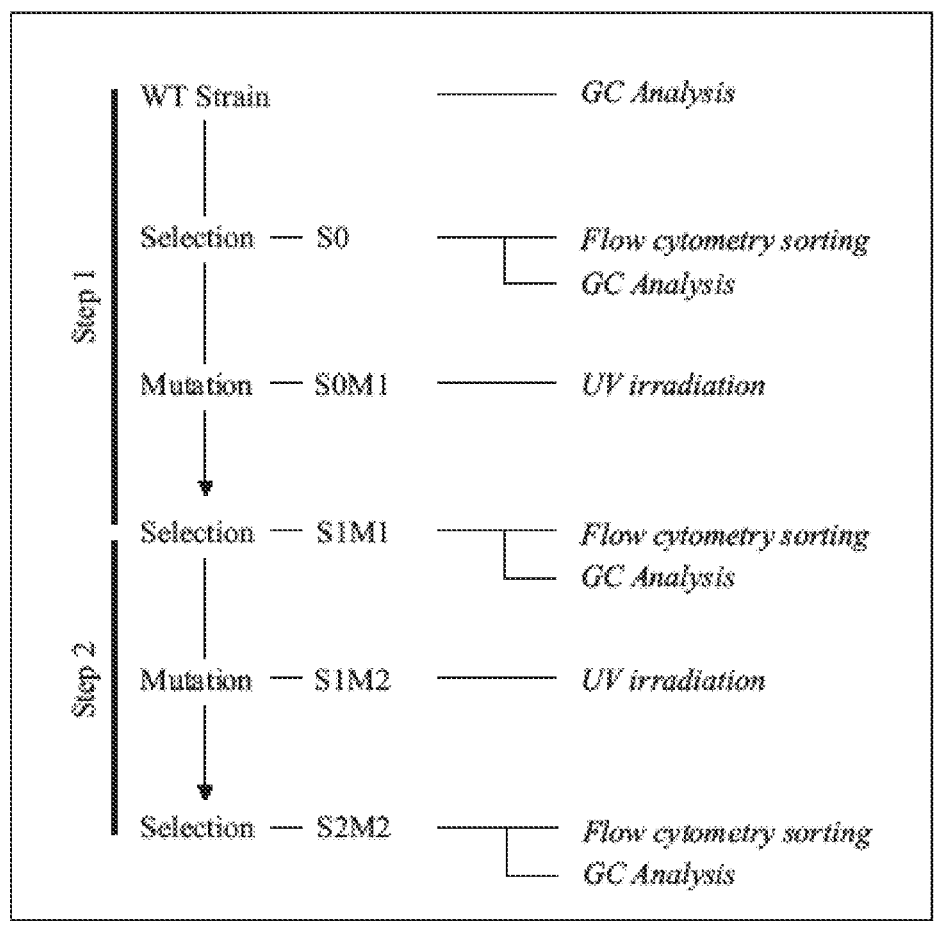
FIG. 1 is a scheme showing the selection-Mutation procedure used to improve the lipid content in the microalgae *Isochrysis affinis golbana*.
Figure 2:
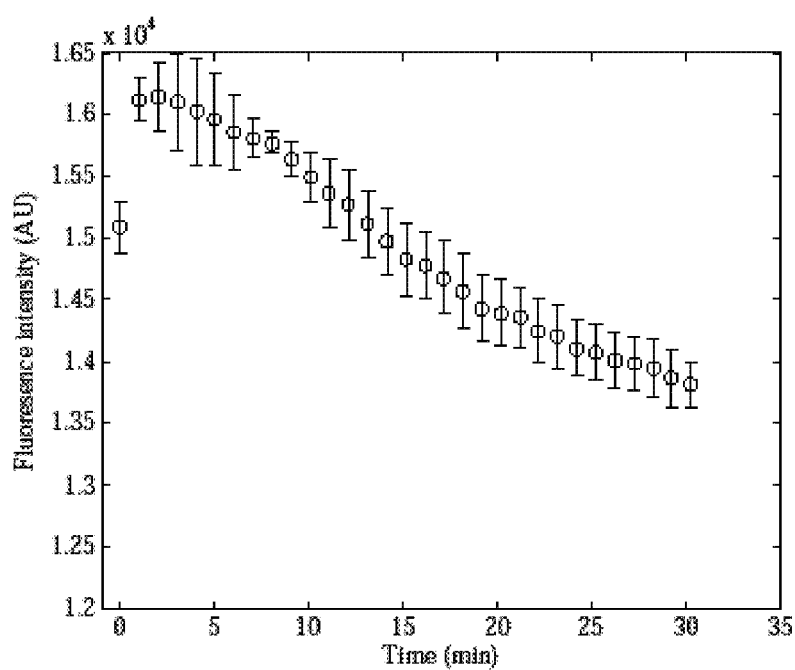
FIG. 2 is a graphic showing the Nile-Red fluorescence decrease versus time. Error bars are standard deviation computed for n=3.
Figure 3:
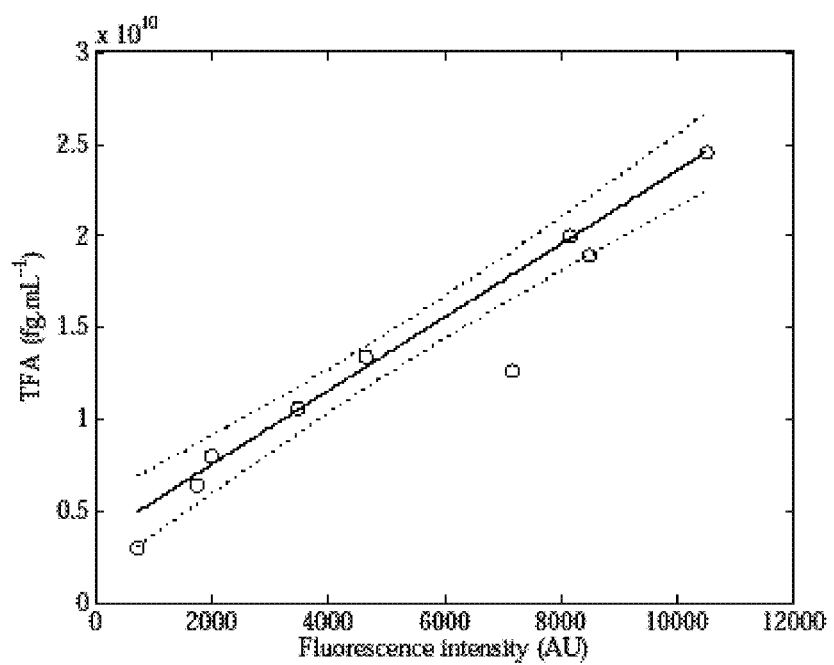
FIG. 3 is a graphic providing the fatty acid concentration (fg mL$^{-1}$) versus the fluorescence intensity. Dashed lines are the 95% confidence interval for regression.
Figure 4:
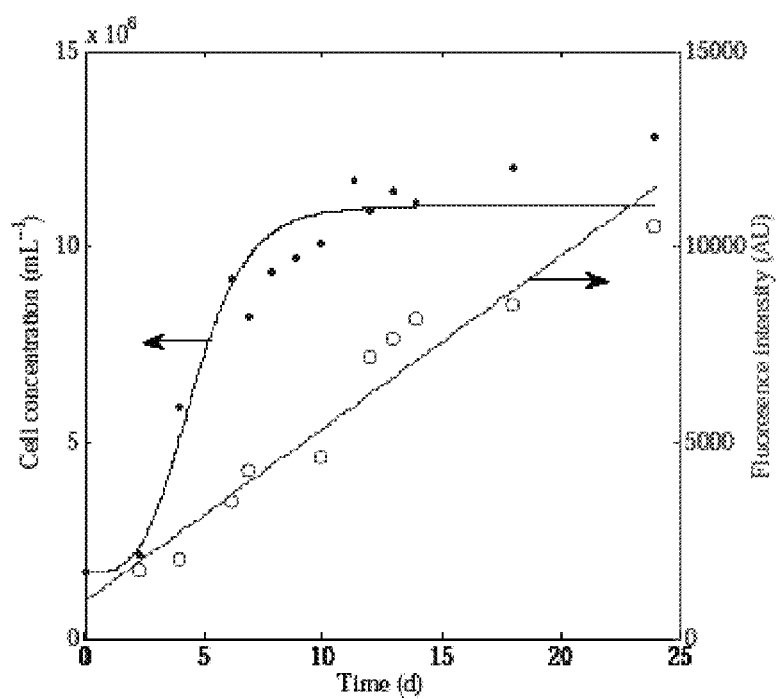
FIG. 4 is a graphic showing the cell concentration and the Nile red fluorescence during a N-limited batch culture. (○) cell concentration, (*) fluorescence.
Figure 5:
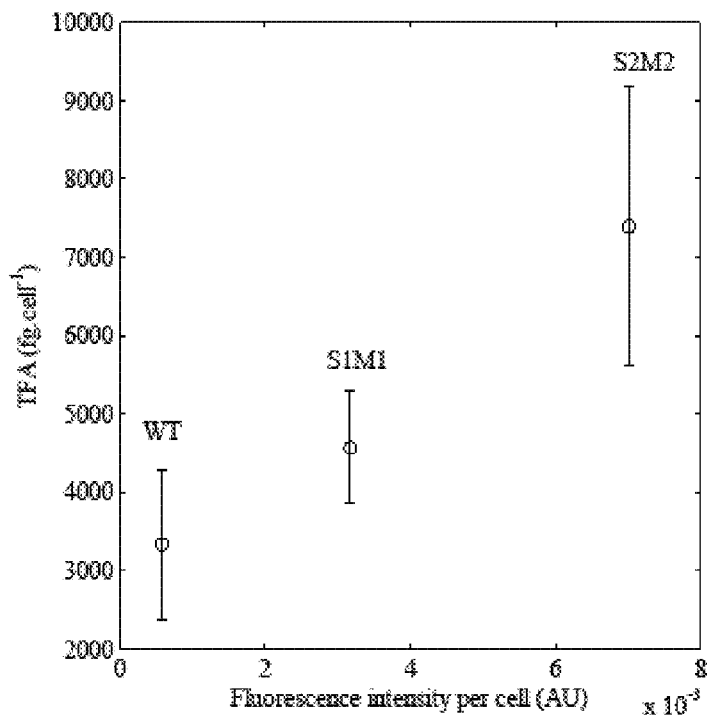
FIG. 5 is a graphic showing the TFA content versus the fluorescence intensity for the three populations dyed with Nile red.
Figure 6:
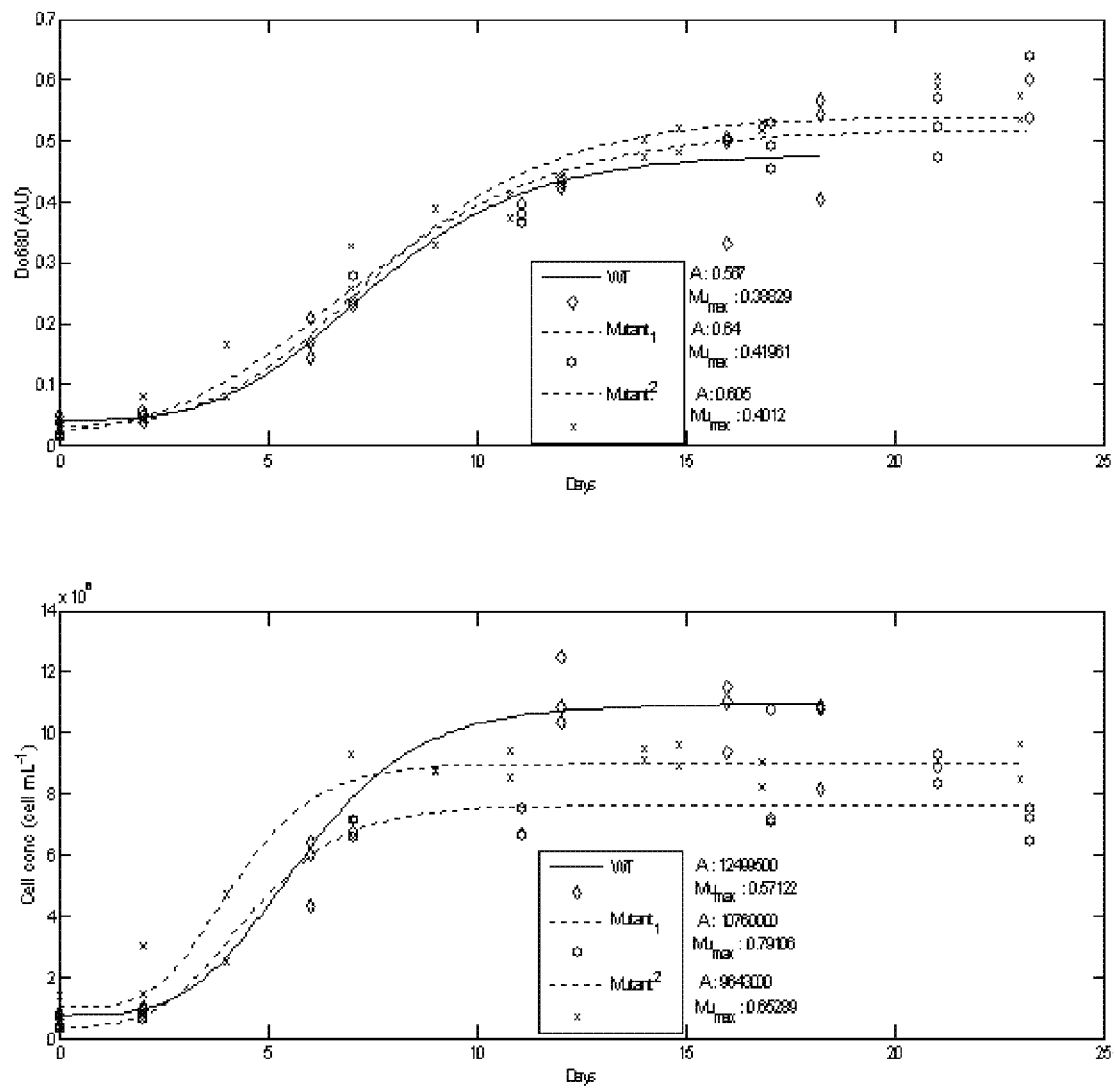
FIG. 6 provides growth curves of *Isochrysis offinis galbana*, wild strain, mutant 1 and mutant 2. On the first growth curve, the Y-axis represents the absorbance in spectrometry. On the second growth curve, the Y-axis represents the cell concentration. Maximum concentration and growth rate (μ) are indicated for each culture.
Figure 7:
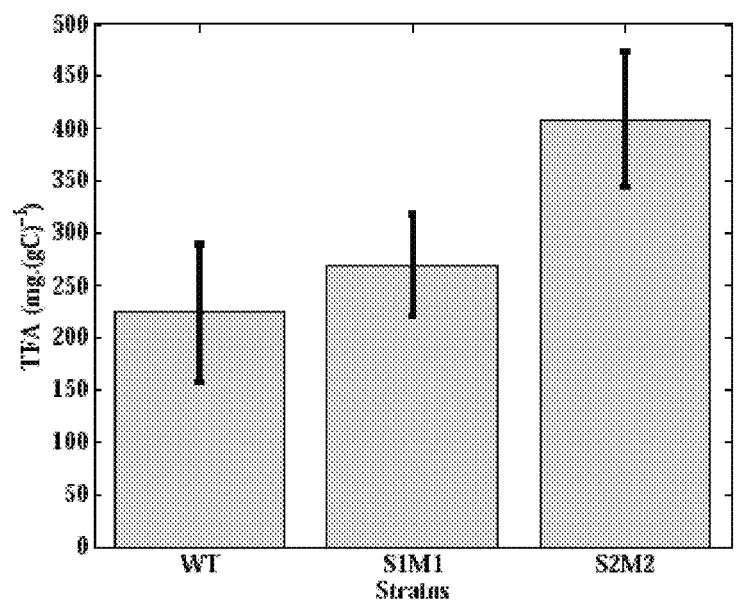
FIG. 7 is a histogram showing total fatty acid for WT, S1M1 and S2M2 cultures.
Figure 8:
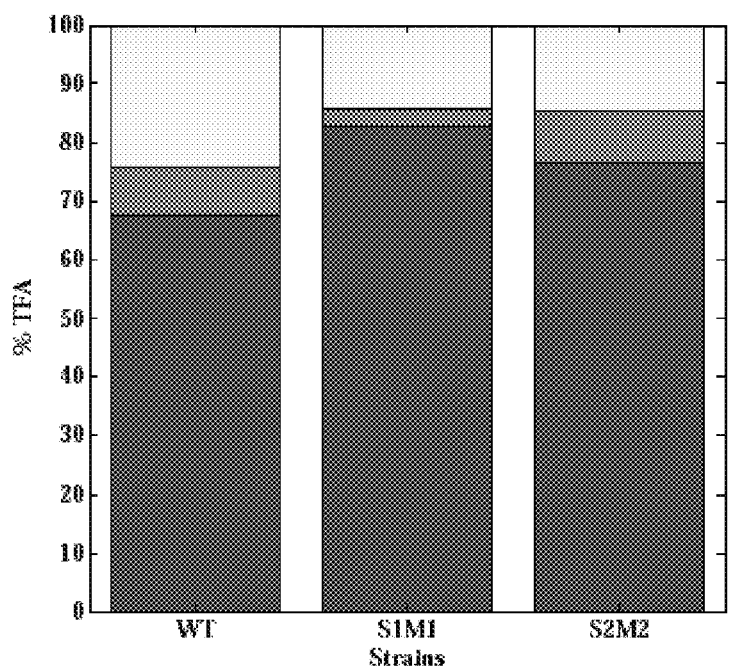
FIG. 8 is a histogram showing distribution of fatty acids among the lipid classes for the three cultures (WT, S1M1 and S2M2). Black: neutral lipids; dark grey: glycolipids; light grey: phospholipids.

As used herein the term "microalgae" refers to a large, heterogeneous group of primitive photosynthetic organisms which occur throughout all types of aquatic habitats and moist terrestrial environments. (Nadakavukaren et al., Botany. *An Introduction to Plant Biology,* 324-325, (1985)).

As used herein, the terms "*Isochrysis* sp Tahitian clone", "*Isochrysis* sp", "*Isochrysis affinis galband*" "*Isochrysis affinis galbana* clone Tahiti", "*Isochrysis affinis galbana* Tahitian clone" and "T-iso" are used interchangeably.

As used herein, the terms "Tahitian clone" and "clone Tahiti" are used interchangeably.

As used herein, the terms "wild strain", "wild type" or "WT" in relation to T-iso refers to an *Isochrysis offinis galbana* strain which is not artificially modified and is isolated from nature.

As used herein, the terms "S1M1" or "mutant 1" refers to an *Isochrysis affinis galbana* strain which has undergone a first selection-mutation cycle according to the present invention.

As used herein, the terms "52M2" or "mutant 2" refers to the microalgal strain of the invention, i.e. having undergone two selection-mutation cycles according to the present invention.

As used herein, the term "mutant" refers to *Isochrysis* sp Tahitian clone that has undergone a mutation, i.e. a change in a nucleic acid sequence (such as a gene sequence) or amino acid sequence, for example as compared to a nucleic acid or amino acid sequence present in a original parental organism of *Isochrysis* sp Tahitian clone as described in the present invention. Mutations can occur spontaneously, or can be introduced, for example using molecular biology methods. In particular examples, a mutation includes one or more nucleotide substitutions, deletions, insertions, or combinations thereof.

As used herein, the term "variant thereof" refers to *Isochrysis* sp microalgae different from the specifically identified *Isochrysis* sp, wherein one or more nucleotides or amino acid residues is deleted, substituted, or added. Variants may be naturally occurring variants, or non-naturally occurring variants. In certain embodiments, variants of the inventive microalga strain possess biological activities that are the same or similar to those of the inventive microalga strain.

As used herein, the term "genetically modified" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein coding sequences such as regulatory sequences as promoters or enhancers.

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms.

As used herein, the terms "fatty acid" and "fatty acids" are used interchangeably.

As used herein, the term "neutral lipids" refers to non-polar lipids. Non-limiting examples of neutral lipids may include triacylglycerol (TAG), steryl esters (SEs), wax ester (WE), and poly(3-hydroxybutyrate) (PHB). Generally speaking, neutral lipids lack charged groups and are therefore unable to integrate into bilayer membranes in substantial amounts. They serve as intracellular storage molecules for sterols, free fatty acids, and diacylglycerols (DAGs).

As used herein, the term "omega-3 polyunsaturated fatty acid(s)" refers to a family of unsaturated carboxylic fatty acids that have in common a carbon-carbon bond in the n-3 position (i.e., the third bond from the methyl end of the molecule). Typically, they contain from about 16 to about 24 carbon atoms and from three to six carbon-carbon double bonds. Omega-3 polyunsaturated fatty acids can be found in nature, and these natural omega-3 polyunsaturated fatty acids frequently have all of their carbon-carbon double bonds in the cis-configuration.

They are referred to as "polyunsaturated" because their molecules have two or more double bonds in their carbohydrate chain.

The PUFA family of oils for food compositions includes: alpha-linoleinc acid (ALA), 18:3 (n-3); stearidonic acid (SDA), 18:4 (n-3); eicosatetraenoic acid, 20:4 (n-3); eicosapentaenoic acid (EPA), 20:5 (n-3); docosapentaenoic acid, 22:5 (n-3) and docosahexaenoic acid (DHA), 22:6 (n-3).

In the following, polyunsaturated fatty acids will be referred to as PUFA, or PUFAs.

DHA (docosahexaenoic acid) (22:6n-3) in the form of, but not limited to, free fatty acid, monoglyceride, diglyceride, triglycerides or ethyl esthers.

As used herein, the term "DHA" refers to docosahexaenoic acid (C22:6), a omega-3 polyunsaturated fatty acid, also known by its chemical name (all-cis-) 4,7,10,13,16,19-docosahexaenoic acid, as well as derivatives thereof. Thus, the term "DHA" encompasses the free acid DHA as well as DHA alkyl esters and triglycerides containing DHA. Hence, in various embodiments, DHA may be in the form of a phospholipid, a triglyceride, free fatty acid, or an alkyl ester.

As used herein, the terms "docosahexaenoic acid", "cervonic acid", "docosahexaenoate" and "DHA" are used interchangeably.

As used herein, the terms "EPA" refers to eicosapentaenoic acid (C20:5), an omega-3 polyunsaturated fatty acid, also known by its chemical name (all-cis-) 5,8,11,14,17-eicosapentaenoic acid, as well as derivatives thereof. Thus, the term "EPA" encompasses the free acid EPA as well as EPA alkyl esters and triglycerides containing EPA. Hence, in various embodiments, EPA may be in the form of a phospholipid, a triglyceride, free fatty acid, or an alkyl ester.

As used herein, the terms "eicosapentaenoic acid", "icosapentenoic acid", "eicosapentenoic acid", "eicosapentaenoate" and "EPA", are used interchangeably.

As used herein, the term "lipid content" refers to the total amount of lipids produced and accumulated by the microalga and that can be extract from said microalga to be used.

As used herein, the term "lipid extract" refers to the lipids that are obtained, isolated and/or derived from microalgae of the invention.

As used herein, the terms "lipid" and "lipid extract" are used interchangeably.

As used herein, the term "harvesting" or "harvest" refers to collecting the lipids produced by the microalgae of the invention by an extraction.

As used herein, the term "algofuel" refers to a fuel made from algal lipid extract for use in motor vehicles. Algofuel is made preferably by a transesterification, a chemical reaction between lipids and alcohol. It can be used alone or blended with conventional petrodiesel in unmodified diesel-engine vehicles (Specification for Biodiesel (B|OO)-ASTM 06751).

As used herein, the term "vehicle" refers to any means of transportation that work on diesel and that could be susceptible to work on algofuel. According to the present invention, the term "vehicle" includes but is not limited to cars, trucks, buses, motorbikes and aircraft.

As used herein, the term "aquaculture" refers to production of any aquatic species produced under aquacultural conditions, such as fish species, including but not limited to salmon or tuna; crustaceans such as shrimp, lobster, crayfish and crabs; molluscs such as bivalves. Preferably, microalgae of the invention are used for feeding oysters.

As used herein, the terms "dietary supplement", "food supplement" and "nutritional supplement" mean any product, containing beneficial nutrients, which is added to the diet for the health of a human being. Dietary supplements include but are not limited to vitamins, minerals, herbs, amino acids, enzymes, and cultures of organisms.

As used herein, the terms "dietary supplement", "food supplement" and "nutritional supplement" are used interchangeably.

As used herein, the term "nutritional deficiencies" refers to the lack of nutrients including but not limited to water, energy (e.g., carbohydrates, proteins, and lipids), proteins (e.g., nitrogenous compounds), minerals, and vitamins.

As used herein, the term "oral administration" refers to the route of administration for medical or nutritional substances through the mouth.

As used herein, the term "topical application" refers to a local application on the skin or on the hair, at, or immediately beneath, the point of application. A topical administration is done directly to the site where it is needed, rather than applied through the circulatory system or through the digestive system.

As used herein, the term "topically applying" refers to direct application to the area of the surface to be affected.

The composition may be applied by pouring, dropping, or spraying, if a liquid; rubbing on, if an ointment, lotion, cream, gel, milk or the like; dusting, if a powder; spraying, if a liquid or aerosol composition; or by any other appropriate means.

As used herein, the term "improvement of skin aspect" refers to the enhancement of the visual aspect and/or of the sensory aspect of the superficial layers of the epidermis. These aspects are enhanced because the skin is better moisturized and consequently appears less dry, with fewer wrinkles, fewer spots and/or with more homogenous and healthy complexion.

As used herein, the term "tablet" refers to uncoated compressed forms of nutritional elements of all shapes and sizes.

Has used herein, the term "capsule" refers to a storage and transportation medium through the alimentary canal of a dietary supplement.

As used herein, the term "caplet" refers to a smooth, coated, oval-shaped tablet.

The term "pills" as used herein refers to both tablets and capsules.

The term "syrup" as used herein, refers to a thick and viscid and oftentimes saturated aqueous solution of a saccharide or a mixture or saccharides and other carbohydrates As used herein, the term "gelcap" otherwise known as "gel caplet," refers to a capsule-shaped dosage form where the active ingredients are dissolved in a liquid that is coated within a gelatin shell for easy swallowing or to have the appearance of easy swallowing.

As used herein the term "paste" refers to a thick, stiff ointment containing at least 20% solids.

As used herein, the term "powder" refers to fine particles that can result from comminution of any dry substance. Generally, powders consist of particles ranging in size from about $0.1\mu$ to about $10,000\mu$, although the most useful pharmaceutical range is approximately from about $0.1\mu$ to about $10\mu$.

As used herein, the term "ointment" refers to a semisolid preparation intended to be applied externally to the skin.

As used herein, the term "cream" refers to an opaque, soft, cosmetically acceptable preparation intended for external application that comprises a water-soluble or cream base and that can be either a water-in-oil (w/o) or an oil-in-water (o/w) type of emulsion.

As used herein, the term "moisturizer" refers to an agent that hydrates the skin. Moisturizers are known in the art. Moisturizers can be used either alone or in combination, e.g., a combination of two or three (or more) different moisturizers can be used.

As used herein, the term "lotion" is used to designate solutions or suspensions that are applied topically. A solution generally is considered as a homogeneous mixture of two or more substances; it is frequently, though not necessarily, a liquid. In a solution, the molecules of the solute (or dissolved substance) are uniformly distributed among those of the solvent.

A solution can be prepared by mixing a solute or dissolved substance uniformly throughout a solvent carrier such as water or organic solvents, such as the alcohols (e.g. ethanol or isopropanol, acetone).

As used herein, the term "suspension" refers to a dispersion (mixture) in which a finely-divided species is combined with another species, with the former being so finely divided and mixed that it doesn't rapidly settle out. In everyday life, the most common suspensions are those of solids in liquid water.

As used herein, the terms "gels" or "jellies" are semisolid systems consisting of suspensions made up of small inorganic particles or large organic molecules interpenetrated by a liquid. The concentration of the gelling agents in a gel typically is less than 10%. In some embodiments the concentration of the gelling agents in a gel is in the about 0.5% to about 2.0% range. A "hydrogel" is an extremely hydrated polymer gel wherein the polymer chain holds many times its weight in trapped water. It contains ingredients that are either dispersible as colloids or soluble in water, including organic hydrogels, natural and synthetic gums, and inorganic hydrogels. In high concentrations, hydrophilic colloids form semisolid gels, also referred to as jellies As used herein, the term "serum" refers to a cosmetic composition comprising more active principle and less water than a cream. Serum has a very fine texture. It penetrates fast into the skin and can be applied to the skin in very small quantities.

The Invention

A first object of the invention relates to a strain of the microalga *Isochrysis*, referred to as *Isochrysis affinis galbana* Tahitian clone, deposited within the Culture Collection of Algae and Protozoa (CCAP (CCAP, Scottish Marine Institute, OBAN, Argyll, PA37 1QA; E-mail: ccap@sams.ac.uk)) under accession number CCAP 927/17 or a mutant or variant thereof.

In a preferred embodiment, the microalgal strain of the invention has a lipid content increased by at least 75% compared to wild strain, preferably at least 100%.

In a preferred embodiment the lipid content of the microalgal strain of the invention comprises at least 70% of neutral lipids, preferably at least 80%.

In a preferred embodiment, the lipid content of the microalgal strain of the invention comprises at least 18% of polyunsaturated fatty acids, preferably at least 20%.

In a preferred embodiment, the microalgal strain of the invention has a growth rate similar to the growth rate of the wild strain.

Preferably, the microalga strain of the invention is not genetically modified.

Another object of the invention relates to a lipid extract obtained from the microalgal strain of the invention.

In a preferred embodiment, the lipid extract of the invention comprises at least 70% of neutral lipids, preferably at least 80%.

In a preferred embodiment, the lipid extract of the invention comprises at least 18% of polyunsaturated fatty acids, preferably at least 20%.

The fatty acid composition (% of total fatty acid) of the wild type (WT), the first mutant (S1M1) and the microalga of the invention (second mutant, S2M2) of *Isochrysis affinis galbana* are disclosed in table 1. (Values presented are means and standard deviation of at least six replicates. SFA: Saturated Fatty acids; MUFA: MonoUnsaturated Fatty acids; PUFA: PolyUnsaturated Fatty acids.)

TABLE 1

| FA (%) | WT | S1M1 | S2M2 |
| --- | --- | --- | --- |
| 14:0 | 24.6 (1.3) | 25.5 (1.1) | 22.1 (1.6) |
| 15:0 | 0.6 (0.0) | — | — |
| 16:0 | 13.5 (0.8) | 15.2 (1.5) | 15.9 (1.6) |
| 18:0 | 0.8 (0.2) | 0.9 (0.2) | 0.7 (0.1) |
| SFA | 39.5 (2.1) | 41.9 (1.2) | 39.7 (0.3) |
| 14:1 n-5 | 0.3 (0.0) | — | 0.2 (0.0) |
| 16:1 n-9 | 1.4 (0.6) | 0.5 (0.3) | 1.9 (1.2) |
| 16:1 n-7 | 3.9 (0.8) | 3.8 (1.6) | 5.1 (1.4) |

TABLE 1-continued

| FA (%) | WT | S1M1 | S2M2 |
| --- | --- | --- | --- |
| 18:1 n-9 | 26.4 (0.7) | 24.2 (3.7) | 28.9 (1.1) |
| 18:1 n-7 | 1.2 (0.2) | 2.0 (0.5) | 1.1 (0.2) |
| MUFA | 33.4 (1.2) | 30.4 (4.6) | 37.9 (2.6) |
| 16:2 n-6 | — | 0.1 (0.0) | 0.1 (0.0) |
| 16:2 n-4 | 0.3 (0.1) | 0.2 (0.1) | 0.2 (0.1) |
| 18:2 n-6 | 3.3 (0.3) | 4.4 (0.7) | 3.8 (0.5) |
| 18:3 n-3 | 2.8 (0.1) | 2.3 (0.5) | 3.1 (0.3) |
| 18:4 n-3 | 9.0 (0.8) | 5.5 (1.3) | 5.8 (1.2) |
| 18:5 n-3 | 1.0 (0.6) | 0.3 (0.1) | 0.4 (0.2) |
| 20:2 n-6 | — | — | 0.1 (0.0) |
| 20:3 n-6 | — | — | 0.1 (0.0) |
| 20:3 n-3 | 0.1 (0.0) | — | 0.2 (0.1) |
| 20:4 n-6 | 0.2 (0.0) | 0.1 (0.0) | 0.1 (0.0) |
| 20:4 n-3 | 0.3 (0.0) | — | 0.3 (0.1) |
| 20:5 n-3 | 0.3 (0.0) | — | 0.2 (0.0) |
| 22:3 n-3 | 0.4 (0.1) | — | 0.2 (0.0) |
| 22:5 n-6 | 1.0 (0.1) | 1.0 (0.2) | 0.8 (0.2) |
| 22:5 n-3 | 0.8 (0.0) | 0.1 (0.0) | 0.9 (0.2) |
| 22:6 n-3 | 6.8 (0.5) | 5.1 (0.9) | 5.0 (1.0) |
| PUFA | 26.4 (1.8) | 19.3 (3.5) | 22.4 (2.8) |

Another object of the invention relates to a method of producing the lipid extract of the invention wherein said method comprises the following steps of:
  a. Culturing a microalgal strain of the invention;
  b. Harvesting the lipid content from said microalgal strain to obtain the lipid extract of the invention.

The method employed to obtain the microalgae of the invention is based on two types of successive operations:
  The selection phase: the aim is to select 10% of the richest microalgal cell population in fatty acids, using cell sorting by flow cytometry (BD facsaria III).
  The mutation phase: The previously selected microalgal cells are exposed to UVC radiations during a time permitting the survival of approximately 10% of the microalgal cells.
  Said operations are made in two successive cycles:
  First cycle: sorting of the wild strain (WT) and mutation and second sorting to obtain the strain S1M1
  Second cycle: mutation of S1M1 in the same conditions than the first cycle and final sorting to obtain the strain S2M2.

The selection is based on lipids and particularly on neutral lipids. The selection requires a flow cytometry sorter with the Nile Red fluorescent stain. The aim of this step is to select migroalgae that are naturally rich in total fatty acids.

The mutation is performed by exposing to a UVC radiation ($\lambda$=254 nm) a thin layer of microalgal cells, in a liquid medium. The exposure dose varies according to the radiation intensity and to the exposure time. The exposure time is determined in order to determine a survival of the microalgae close to 10% (19% for an exposure time of 12 minutes and 4% for an exposure time of 32 minutes). These conditions permit a reduction of the population of over 80% compared with the initial microalgal population. This reduction is necessary to obtain the proof of a mutagenic effect.

For each selection-mutation cycle, the exposure to the radiation is done in triplicate.

12 mL of the microalgal culture are spread in a petri dish (diameter 100 mm) and exposed under an UVC light ($\lambda$=254 nm), 13 cm away, during 12 or 32 minutes.

Microalgal cells are put back in culture, in erlenmeyer flask of 50 mL, enriched with Conway's medium (1 mL/L) and maintained in the dark during a night to avoid photoreactivation.

Cultures are stored in a culture room at 21° C. and under an irradiance of 80 μmol·m$^{-2}$·s$^{-1}$ to permit the resumption of the microalgal cells proliferation.

After a waiting time comprised between 18 and 30 days, depending on the mutation level the volume is poured in another Erlenmeyer in which the volume of the culture is adjusted at 250 mL by the addition of culture medium.

When there is enough biomass, an aliquot of each culture is stained with Nile Red (1 μL/mL of culture) and sorted with the flow cytometer (excitation λ=525 nm; emission (λ=580 nm) to select the richer microalgal cells in neutral lipids, that represent 10% of the population.

Microalgal cells resulting from each one of the selection-mutation cycle (S1M1 or S2M2) are put back in culture under conditions of nitrate deficiency, known to favour lipid production in microalgae.

A characterization of their maximum growth rate and cellular size is done during this stage.

When the culture reaches the stable phase, the fatty acids of the extract are separated into the different classes of lipids and analyzed in triplicate by gas chromatography.

Another object of the invention relates to the use of the microalgal strain of the invention for producing the lipid extract of the invention.

Another object of the invention relates to the use of the microalgal strain of the invention in aquaculture.

Preferably, the microalgal strain of the invention is a new variety of microalgae because it presents long term stability.

Another object of the invention relates to the use of the lipid extract of the invention for producing algofuel.

In a preferred embodiment, the algofuel of the invention is for vehicles.

Another object of the invention relates to the use of the lipid extract of the invention for producing dietary supplements.

In a preferred embodiment, dietary supplements of the invention are for oral administration.

In a preferred embodiment, dietary supplements of the invention are for nutritional deficiencies and/or improvement of skin aspect.

In a preferred embodiment, dietary supplements of the invention are under the form of capsule, tablet, elixir, solution, syrup, powder and/or pill.

Another object of the invention relates to the use of the lipid extract of the invention for producing cosmetic compositions.

In a preferred embodiment, cosmetic compositions of the invention have a topical application.

In a preferred embodiment, cosmetic compositions of the invention are for moisturizing skin and improving skin aspect.

In a preferred embodiment, cosmetic compositions of the invention are under the form of cream, ointment, serum, body and/or hair oil, lotion, body and/or hair milk and/or gel.

The following experiments are offered to illustrate embodiments of the invention and should not be viewed as limiting the scope of the invention.

EXAMPLES

Example 1

Selection-Mutation Protocol a) Microalga Strain

*Isochrysis affinis galbana* clone Tahiti (T-Iso) was provided by the CCAP Culture Center of Algae and Protozoa and verified in the laboratory by rDNA 18S sequencing as being CCAP 927=14.

b) Cultural Conditions

All the experimental cultures were performed under nitrate limiting conditions to enhance lipid production and were run in triplicates conditions. Cultures were grown in 2-L flasks and bubbled with 0.22 μm filtered-air. Once filled with the culture medium, flasks were sterilized for 20 min at 120° C. The enrichment solution consisted of 1 mL·L$^{-1}$ of Conway (Walne, 1966) with nitrate concentration being 0.6 mM, i.e. half of the standard Conway medium. The cultures were maintained at a constant temperature set to 21° C. and under a constant 80 μmol·m$^2$·s$^1$ irradiance. Initial cell concentration was 5.10$^5$ cell·mL$^{-1}$.

c) Cell Counting

Cell counting was undertaken by means of a Malassez counting cell and image analysis (with the SAMBA software). Cell concentration was also assessed by absorption measurement at λ=680 nm ($A_{680}$) and λ=800 nm ($A_{800}$) as measured with a Bio-Tek pQuant Universal Microplate Spectrophotometer. For growth rate computation, the Gompertz model modified by Zwietering et al. (1990) was fitted to the experimental data, according to equation:

$$\ln\frac{X}{X_0} = A \times \exp\left(-\exp\left(\frac{\mu_{max} \times \exp(1)}{A} \times (l-t) + 1\right)\right)$$

Where A is the maximal cell concentration, $\mu_{max}$ is the maximum specific growth rate, $x_0$ is the initial cell concentration at $t_0$, x is the cell concentration at t and l is the lag time defined as the t-axis intercept of the tangent at the inflection point.

d) Cell Size Analysis

The cell size measurements were performed with a Coulter Counter Multisizer 3 (Beckman Coulter, High Wycombe, U.K). Before measurement, samples were diluted to with sterile seawater, and then cell size, given as sphere diameter, was calculated using the MS-Multisizer 3 software (Beckman Coulter, High Wycombe, U.K.).

e) Mutation Procedure

Unlike many other species, T-Iso can hardly be cultured on gelose. Hence, the irradiation has to be performed in liquid media. Mutation was induced using a λ=254 nm UVC lamp (340 μW·cm$^{-2}$, Bioblock). The exposure was carried out in a sterile Petri dish (100 mm) where 12 mL of culture were deposited (this volume made possible a complete spreading and limited self-shading). The distance between the lamp and the dish was set to 13.5 cm (distance related to the configuration of the lamp) and irradiation lasted for 1 to 32 min. A set of preliminary experiments aimed at establishing a proper UV-dose for mutagenesis. We assumed that a 10% survival rate for the irradiated cells was associated to a substantial mutagenic effect. We therefore tested different irradiation periods (1, 2, 3, 4, 6, 8, 9, 12, 16 and 32 min) and measured the cell concentration and absorption $A_{680}$ versus time after UV exposure. The survival rate was computed as the ratio of the minimum cell concentration measured subsequently to UV exposure to the initial cell concentration or as the corresponding ratio for $A_{680}$.

Each mutation operation was carried out on triplicate Petri dishes. After exposure, cells were transferred into a 50 mL Erlenmeyer filled with filtered-sterilized and Walne-enriched seawater. Cultures were subsequently maintained in the dark for 24 hours to avoid photo reactivation. Then, cultures were placed in a culture cupboard at 21° C. and under a 80 μmol·m$^{-2}$·s$^{-1}$ irradiance.

f) Nile Red Staining

The 9-dietylamino-5H-benzo(a)phenoxazine-5-one (Nile-Red) is a lipophilic fluorochrome, (Greenspan et al., 1985), allowing a fast staining of neutral lipids. In a hydrophobic medium, the lipid corpuscles appear yellow-stained. Excitation wavelength is λ=525 nm and emission wavelength is λ=580 nm. The dye was dissolved in acetone so as to obtain a 250 μg·mL$^{-1}$ concentration. This solution was added to the culture samples at a rate of 1 μL·mL$^{-1}$.

The correlation between the Nile-Red fluorescence and the fatty acid concentration was assessed as follow: a N-limited batch culture was sampled periodically for twenty-four days, until stationary phase was achieved. Samples were analyzed for both total fatty acid concentration in the culture, with gas chromatography and Nile-Red fluorescence as measured with a microplate spectrofluorimeter (Tecan Safire).

g) Selection-Mutation Procedure

Batch cultures in stationary phase under nitrate starvation were used and processed with a Facsaria III Cytometer (Becton-Dickinson) fitted with an automatic sorting device. Sheath fluid was PBS (Phosphate Buffer Saline). Laser emission wavelength and filter were set as specified above. As Nile Red is not referenced, phycoerythrine (λ=560 nm) was taken instead as a reference. A consequent agitation was necessary before passing samples through the cytometer as well as a filtration on a mesh in order to remove the aggregates. Nile Red was added immediately before the culture was pumped into the cytometer. Two runs in the cytometer made it possible to check for the quality of the cell selection. The sorted cells were recovered in 3 mL sterile box. At first appearance of recovery, algal cells were transferred into a 50 mL Erlenmeyer until cell concentration reached 1·10$^6$ cell·mL$^{-1}$, then transferred in a 250 mL Erlenmeyer in order to obtain the necessary biomass to proceed to the subsequent analyses.

The selection-mutation procedure consisted in two successive cycles, as follows: the wild type strain (WT) was first sorted by Flow Cytometry: the 10% of the cells showing the strongest fluorescence intensity were selected and picked out by the automatic device. The triplicate cultures that were inoculated with the sorted cells were called S0. Cells were then analyzed for their TFA content once stationary phase under N starvation was achieved. Three sub-samples of the S0 culture were then exposed to a 32 min UV irradiation as described in the mutation procedure section. After a 30 days delay, needed for growth recovery, the resulting S0M1 population was sorted again using flow cytometry for the 10% cells showing the strongest fluorescence intensity. The resulting S1M1 population was again allowed to recover for 30 days and was analysed for cell TFA content once stationary phase under N starvation was achieved. During the second cycle, the S1M1 population was again exposed to a 32 min UV irradiation as previously described and the resulting S1M2 population was then sorted by flow cytometry after recovery, resulting in the S2M2 population. The S2M2 TFA content was finally analyzed once stationary phase under N starvation was achieved.

The survival rates for cells and the recovery frequency for cultures that have been exposed to UV radiation are disclosed in table 2. (Survival rates were estimated on the basis of $A_{680}$ measurements. Data from 4 independent sets of experiments are presented with standard deviation in brackets.)

TABLE 2

| Irradiation period (min) | Survival rate (%) | Recovery frequency (%) | Replicates |
|---|---|---|---|
| 0 | 100 (0) | 100 | 10 |
| 1 | 100 (—) | — | 1 |
| 2 | 100 (—) | — | 1 |
| 3 | 53 (20) | 75 | 8 |
| 4 | 60 (—) | — | 1 |
| 6 | 50 (15) | 50 | 8 |
| 8 | 47 (—) | — | 1 |
| 9 | 40 (8) | 50 | 8 |
| 12 | 28 (11) | 44 | 9 |
| 16 | 21 (6) | 75 | 3 |
| 32 | 19 (—) | 33 | 3 |

Cell diameter and maximum growth rate ($\mu_{max}$) for the three cultures (WT, S1M1 and S2M2) are disclosed in table 3. (Values presented are means with standard deviations in brackets. Means were compared by ANOVA (α=0.05) and groups with the same letter indicate no significant difference)

TABLE 3

| Culture | $\mu_{max}$ (d$^{-1}$) | mean cell diameter (μm) | Number of replicates |
|---|---|---|---|
| WT | 0.40$^a$ (0.08) | 4.76a (0.56) | 5 |
| S1M1 | 0.45$^a$ (0.09) | 4.94a (0.55) | 6 |
| S2M2 | 0.38$^a$ (0.05) | 4.98a (0.52) | 6 | h) Fatty Acids Analyses

Gas Chromatography (GC) analyses of the total fatty acids were carried out on triplicates. Three successive samples were taken every two days from the onset of the stationary phase for the nitrogen-depleted batch cultures. Sample volume was adapted so as to get a total population of 1.5 10$^8$ cells in the sample, which allowed GC analyses in the proper range. Each sample was filtered on 450° C. pre-combusted GF/C filter (Whatman, diameter 47 mm), then deposited in a glass bottle filled with 6 mL of Folch reagent and deep-frozen (−80° C.). Lipid class separation was realized by column chromatography. A borosilicate Pasteur pipette (0.5 cm internal diameter and 9 cm long) was plugged with silanized glass wool and dry-loaded on 4.5 cm with 600 mg of silica gel 60 (Merck 0.063-0.200 mm, 6% H$_2$O). The column was conditioned with 5 mL of chloroform, then 3 mL of lipid extract (evaporated under nitrogen) were subjected to column chromatography. The neutral lipids, glyco- and phospholipids were eluted by chloroform (10 ml), acetone (20 ml) and methanol (15 ml), respectively. Solvents were evaporated and the lipid classes were estimated by weighting with a microbalance (Satrorius MC210P). All fractions were kept in Folch reagent and frozen (−20° C.) until analyses.

For fatty acid analysis, total lipid extract (2 mL) as well as lipid class fractions were evaporated under nitrogen and transmethylated by direct transesterification with BF3-methanol at 100° C. for 10 min (Metcalfe and Schmitz, 1961). 1 mL of distilled water and 1 mL of hexane were added and vortexed. The upper organic phases, containing fatty acid methyl esters (FAMEs), were collected and assayed by GC-FID. FAMEs quantification was calculated compared to the C17 internal standard (Sigma) by GC-FID using a gas chromatograph (Auto system Gas Chromatography, Perkin-Elmer), equipped with an autosampler and fitted with a split/splitless injector and flamme ionisation detector. The separation was carried out with a BPX-70 capillary column (60 m long, 0.25 mm internal diameter, 0.25 lm film thickness; SGE, Austin, USA), containing a polar stationary phase (cyanopropyl-siloxane).

In order to express the fatty acid content on a per carbon basis, particulate carbon was measured using a CN elemental analyzer (Thermoelectron). Methionine, aspartic acid and nicotinamide with various N and C percentage were used for calibration. Samples were collected on a precombusted GF/C filter (Whatman, 25 mm diameter). The filters were deposited in limp glass, placed in steam room and dried at 75° C. for 24 hours, then deep-frozen until analysis.

TFA content, C quota and cell diameter for the three cultures (WT, S1M1 and 52M2) are disclosed in table 4. (Values presented are means with standard deviations in brackets. Means were compared by ANOVA ($\alpha=0.05$) and groups with the same letter indicate no significant difference)

TABLE 4

| Strain | TFA (pg · cell$^{-1}$) | TFA (mg · gC$^{-1}$) | C quota (pg · cel$^{l-1}$) | Number of replicates |
|---|---|---|---|---|
| WT | 3.3$^a$ (0.9) | 224$^a$ (66) | 15.3$^a$ (3.7) | 9 |
| S1M1 | 4.6$^a$ (0.7) | 269$^a$ (49) | 17.4$^a$ (3.7) | 6 |
| S2M2 | 7.4$^b$ (1.8) | 409$^b$ (64) | 18.4$^a$ (5.1) | 13 |

To conclude, the combination of UV mutagenesis to flow cytometry sorting permits to enhance the lipid content of *Isochrysis affinis galbana* by 80%. Particularly, neutral lipids content is increased by 100% compared to the wild strain. However, the novel microalgal strain obtained by the method of the invention has the same growth rate than the wild strain.

Example 2

Oysters Feeding

Microalgae such as *Isochrysis affinis galbana* of the invention are used for feeding oysters during the two main stages of their development.

a) Genitors Conditioning

During this stage, algae that are used for feeding genitors comprise but are not limited to *Isochrysis galbana* and *Isochrysis affinis galbana*, *Tetraselmis* (including *T. chuii*, *T. tetrahele* and *T. suecica*), *Pavlova lutherii*, *Chaetoceros muelleri*, *Thalassiosira* (including *T. pseudonana* and *T. weisfloggii*) and *Skeletonema costatum*.

It is advisable to feed oysters with a combination of different algae such as those describes previously. However, some species of microalgae should not be employed because they are indigestible (*Chlorella* sp.) or because of their lack of unsaturated fatty acids (*Dunaliella tertiolecta*).

The daily food ration necessary for the conditioning depends on the dry mass of flesh of an adult and is calculated in dry mass of algae. It fluctuates from 2 to 4% of the flesh dry mass at the beginning of the conditioning.

Thus, a 3% daily food ration for an adult having a dry mass of flesh of 0.759 is 0.0225 g of algae dry mass.

b) Larval Rearing

Larvae obtained from the fecundation of the genitors' gametes, called D-larvae, are collected and counted.

During the rearing stage, larvae are fed with unicellular algae.

Algae used for feeding larvae comprise but are not limited to Diatoms (*Chaetoceros muelleri*, *Chaetoceros calcitrans*, *Thalassiosira pseudonana*) and Flagellates (*Isochrysis galbana*, *Isochrysis affinis gaolbana*, *Pavlova lutherii* and *Tetraselmis* (only for larvae having a length bigger than 120 μm)).

Unicellular algae are used in combination because a ration containing a combination of diatoms and flagellates permits an enhancement of the growth and the development of larvae, compared to a ration containing only one species of algae. Combinations of algae also permit to improve metamorphosis yield and future growth and survival of oyster spats.

Thus, the appropriate food for D-larvae and first larval stages (shell length lower than 125 μm) is a combination of:
  One of the following Diatoms:
    *Chaetoceros calcitrans* or
    *Thalassiosira pseudonona* (for larvae having a shell length bigger than 55 μm) or
    *Chaetoceros muelleri* (for larvae having a shell length bigger than 90 μm).
  One of the following flagellates:
    *Isochrysis galbana* or
    *Isochrysis offinis galbana* or
    *Pavlova lutheril*

For larvae having a shell length bigger than 120 μm, bigger flagellates can be used such as *Tetraselmis* spp. (*T. chuii*, *T. suecica*, *T. tetrahele*, etc.).

Daily food rations are expressed in number of algal cell per microliter (cells per μL) or per milliliter (cells per mL) of the volume of the culture of the larval tray.

The quantity of each species in a ration is calculated on the basis of the equivalent volume. Approximately: 1.0 cell of *Isochrysis galbana*, *Isochrysis affinis galbana* or *Pavlova lutherii*=
  0.1 cell of *Tetraselmis* sp., or
  0.75 cell of *Chaetoceros muelleri*, or
  1.0 cell of *Thalassiosira pseudonana*, or
  2.25 cells of *Chaetoceros calcitrans*.

Thus, a daily food ration for the first larval stages of *Crassostrea gigas* (and most of the other species of oysters) wherein the target cellular density is 100 cells equivalent *Isochrysis galbana* per μL is obtained by one of the following combinations:
  125 cells per μL *C. calcitrans*+50 cells per μL *I. galbana*;
  37.5 cells per μL *C. muelleri*+50 cells per μL *P. lutherii*;
  50 cells per μL *T. pseudonana*+50 cells per μL *P. lutherii*

The flagellate *P. lutherii* as a similar profile to *I. galbana* but contains more DHA. *Isochrysis affinis* galbana contains 50 to 70% of the DHA content of *I. galbana* when they are cultivated in the same conditions.

However, *Isochrysis affinis* galbana is more used in hatchery than the other algae because it is easier to produce all the year round, is tolerant to high temperatures and has a growth rate higher than the other algae.

Replacing species for *Tetraselmis* are *Pyramimonas* such as *P. obovata* and *P. virginica*. They have PUFA profiles intermediate between *Tetraselmis* and *Isochrysis* but they are difficult to produce during some time of the year.

c) Calculation of Food Ration

Algal volumes that are added to larval tray to have the recommended cellular density are calculated according to equation:

$$\text{Volume [L] to add} = \frac{\text{Desired cellular density [cells per } \mu\text{L]} \times V[L]}{\text{algal cellular density at the time of the harvest [cells per } \mu\text{L]}}$$

V=volume of the larval cultures in the tray

In the following calculation, regime and cellular density to add are:
  37.5 cells per μL *C. muelleri*+50 cells per μL *P. lutherii*
  Cellular densities of harvested algae are:
  *C. muelleri* 4 800 cells par μl;
  *P. lutherii* 8 900 cells par μl.
  Volume of the larval culture is 800 L Calculation:
Volume of *C. muelleri* to add: 37.5×800/4 800=6.25 L
Volume of *P. lutherii* to add: 50.0×800/8 900=4.49 L Example 3

Long Term Stability

Between 2009 and 2011, the microalgae strain of the invention (S2M2) was transplanted 34 times. The C quota was measured to follow the strain characteristics. The results are presented in table 5.

TABLE 5

| Year | C quota (mg/g) |
|------|----------------|
| 2009 | 409            |
| 2011 | 414            |

These results show that there is a long term stability of the strain of the invention. Thus, a varietal selection of the strain of the invention took place.

We claim:

1. A strain of the microalgae *Isochrysis affinis galbana* Tahitian clone, deposited within the Culture Collection of Algae and Protozoa (CCAP) under accession number CCAP 927/17, wherein said microalgae has a lipid content increased by at least 75% compared to the wild type *Isochrysis affinis galbana* clone Tahiti (T-iso) CCAP accession no. 927/14.

2. The microalgal strain of claim 1, wherein said lipid content comprises at least 70% of neutral lipids.

3. The microalgal strain of claim 1, wherein said lipid content comprises at least 18% of polyunsaturated fatty acids.

4. The microalgal strain of claim 1, wherein said microalgae has a growth rate similar to the growth rate of the wild type *Isochrysis affinis galbana* clone Tahiti (T-iso) CCAP 927/14.

5. A method of producing a lipid extract, comprising:
   a. Culturing the microalgal strain according to claim 1; and
   b. Harvesting the lipid content from said microalgal strain to obtain the lipid extract.

6. A method of producing an aquatic species under aquacultural conditions, comprising feeding to the aquatic species a nutritionally effective amount of the microalgal strain according to claim 1.

7. The microalgal strain of claim 1, wherein said microalgae has a lipid content increased by at least 100% compared to the wild type *Isochrysis affinis galbana*.

8. The microalgal strain of claim 1, wherein said lipid content comprises at least 80% of neutral lipids.

9. The microalgal strain of claim 1, wherein said lipid content comprises at least 20% of polyunsaturated fatty acids.

* * * * *